(12) United States Patent
Long et al.

(10) Patent No.: US 7,595,880 B2
(45) Date of Patent: Sep. 29, 2009

(54) OPTICAL DATA CAPTURE AND QUALITY ASSURANCE

(75) Inventors: Gerald A. Long, Greensboro, NC (US); Kenneth A. Ingold, Greensboro, NC (US); A. Leonard Rhyne, Winston-Salem, NC (US)

(73) Assignee: Lorillard Licensing Company, LLC, Greensboro, NC (US)

( * ) Notice: Subject to any disclaimer, the term of this patent is extended or adjusted under 35 U.S.C. 154(b) by 506 days.

(21) Appl. No.: 11/595,168

(22) Filed: Nov. 8, 2006
(Under 37 CFR 1.47)

(65) Prior Publication Data
US 2007/0144545 A1 Jun. 28, 2007

Related U.S. Application Data

(60) Provisional application No. 60/735,154, filed on Nov. 8, 2005.

(51) Int. Cl.
*G01N 21/84* (2006.01)
(52) U.S. Cl. ........................................ 356/429; 356/431
(58) Field of Classification Search .......... 356/426–431
See application file for complete search history.

(56) References Cited

U.S. PATENT DOCUMENTS

| | | | | | |
|---|---|---|---|---|---|
| 3,972,624 | A | * | 8/1976 | Klein et al. | 356/431 |
| 4,040,748 | A | * | 8/1977 | Belleson et al. | 356/431 |
| 4,187,862 | A | * | 2/1980 | Cohn | 131/349 |
| 5,339,150 | A | * | 8/1994 | Hubble et al. | 399/49 |
| 7,116,750 | B1 | * | 10/2006 | Iaquinta et al. | 378/53 |

* cited by examiner

*Primary Examiner*—Gregory J Toatley, Jr.
*Assistant Examiner*—Jarreas C Underwood
(74) *Attorney, Agent, or Firm*—Locke Lord Bissell & Liddell LLP

(57) ABSTRACT

A method and system for capturing and analyzing an image of a moving web of cigarette paper having a plurality of transverse banded regions. The captured images of the moving web of cigarette paper are analyzed to determine various characteristics of a population of cigarettes made with the cigarette paper. Each captured image is decomposed into a matrix of grey scale values associated with individual pixels of the image. The values are further processed to determine a width of a banded region on the cigarette paper. The average widths of banded regions, as well as the standard deviation of widths may be analyzed and correlated to freeburn and ignition propensity characteristics of a population of cigarettes formed from the measured cigarette paper.

26 Claims, 10 Drawing Sheets
(1 of 10 Drawing Sheet(s) Filed in Color)

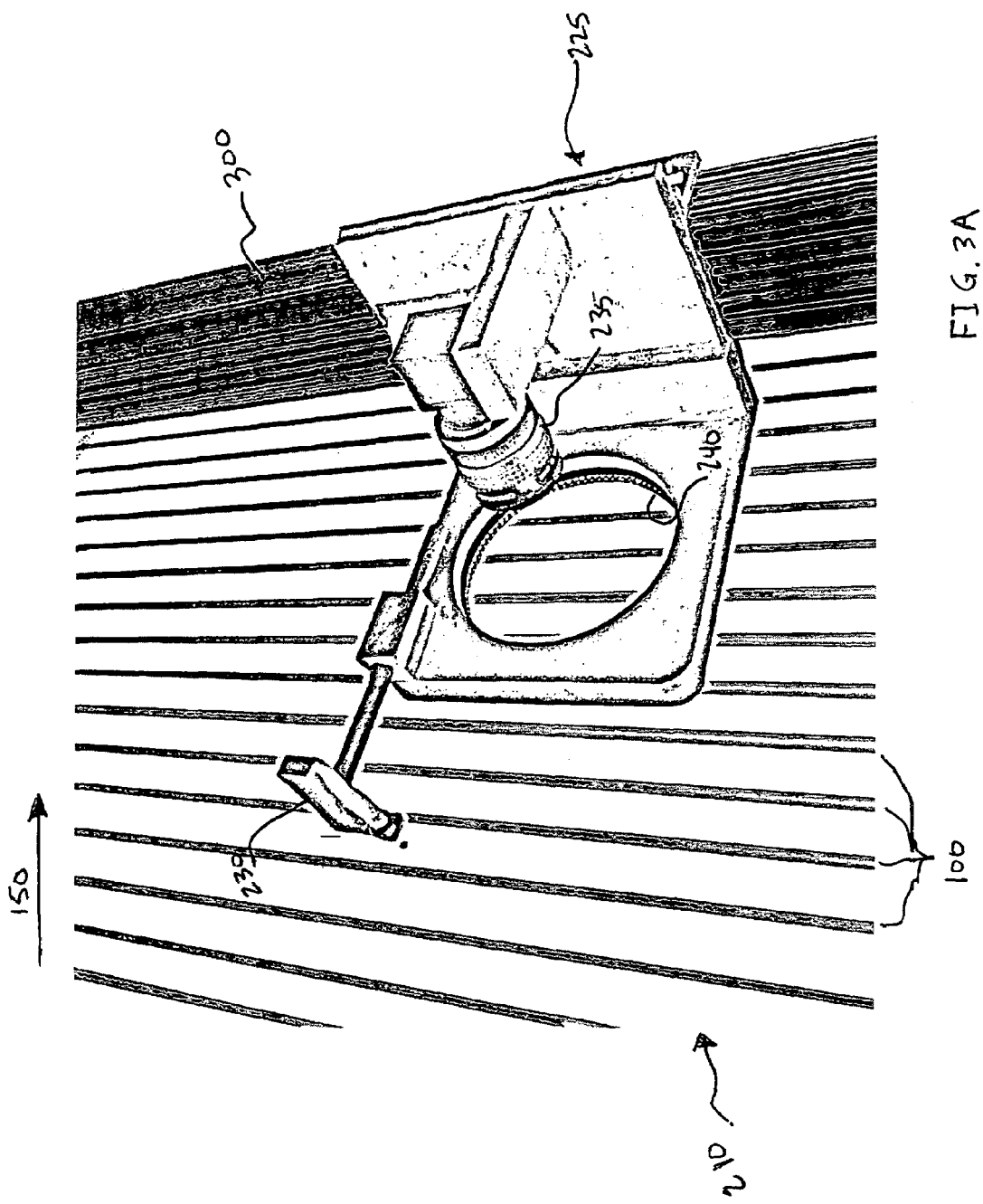

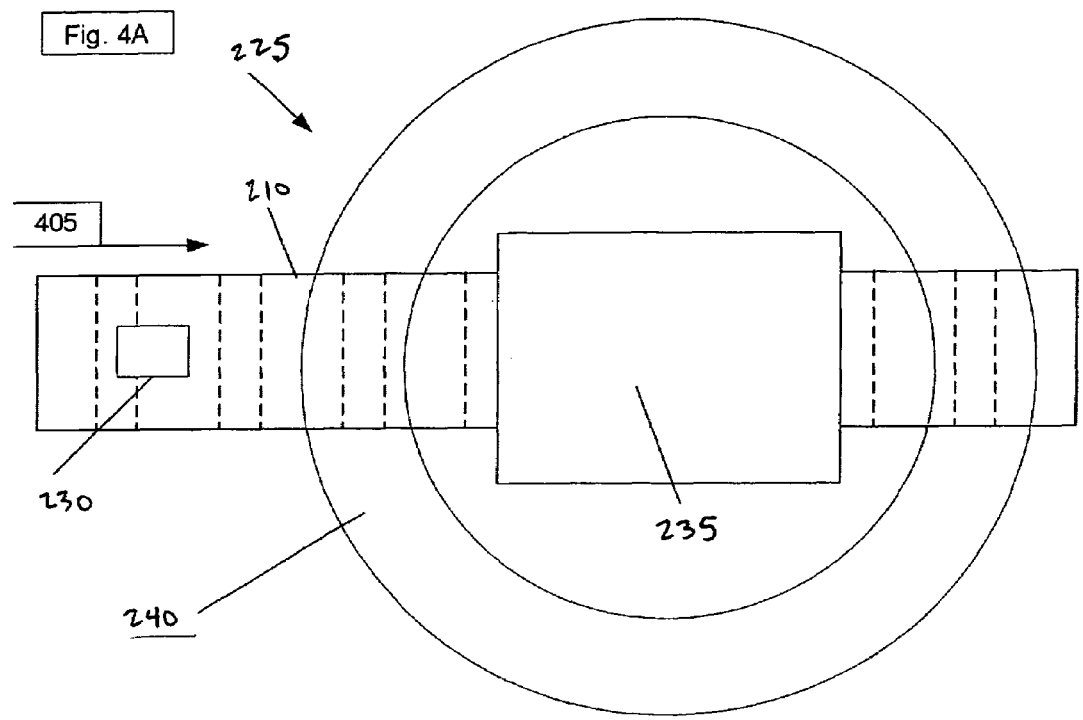
FIG. 4B
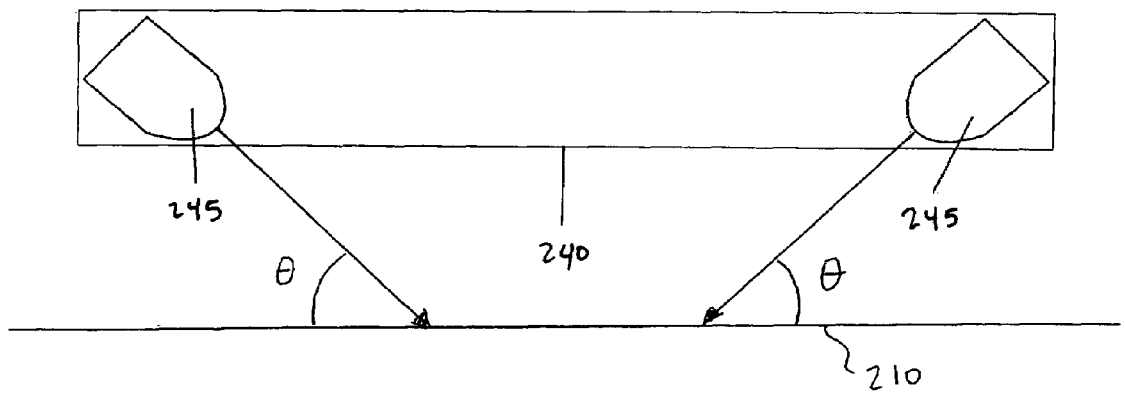

OPTICAL DATA CAPTURE AND QUALITY ASSURANCE

FIELD OF INVENTION

The present invention relates generally to the field of optical data capture and analysis. More specifically, the invention relates to a system and method for capturing image data of a product, analyzing the image data and determining product characteristics based on the analyzed image data. An embodiment of the invention is directed to capturing and analyzing image data for determining characteristics of cigarette wrappers, especially those used in cigarettes having reduced Ignition Propensity (IP) and acceptable freeburn characteristics.

BACKGROUND INFORMATION

It has been found that under certain circumstances, cigarettes may tend to ignite combustible substrates if the cigarette is placed on the substrate. For obvious fire safety reasons, it is desirable for cigarettes to have reduced IP when placed on a combustible substrate, so that they will tend to self-extinguish or not ignite the substrate. Government bodies have recently begun to enact legislation requiring cigarettes to meet reduced IP standards. In addition, it is important from a consumer acceptability standpoint that cigarettes having reduced IP characteristics also have acceptable freeburn characteristics when freely suspended in a static state so that they will not otherwise self-extinguish.

U.S. Pat. No. 6,837,248, which is incorporated herein by reference in its entirety, describes and claims cigarettes having reduced IP characteristics through the provision of one or more circumferential banded regions of reduced permeability on the wrapper. FIG. 1 shows a plan view of a bobbin of reduced IP cigarette paper having transverse banded regions 100. FIG. 2 shows a cigarette 110 having a filter 120 and a tobacco rod surrounded by a wrapper 130 formed from the reduced IP paper of FIG. 1.

It has been found that the ability of these cigarettes to exhibit acceptable reduced IP and freeburn characteristics depends in part on the permeability of the cigarette wrapper in the circumferential banded regions, the composition of the material applied in the banded regions, the width of the banded regions and the spacing between adjacent banded regions. These parameters can be difficult to control since the base paper is typically moving at speeds of 500 feet per minute or more when the banding substance is applied to the paper. For quality assurance and legal compliance, it is important to ensure that the banded cigarette wrapper meets specifications and ignition propensity and/or freeburn performance requirements.

Accordingly, it is an objective of the present invention to provide a system and method for inspecting and analyzing the characteristics of cigarette wrappers to assure that the wrapper meets manufacturing specifications.

SUMMARY OF THE INVENTION

The present invention provides a method and system for capturing an image of cigarette paper during the band application process or after the banded material has been applied. The image is analyzed in order to determine the integrity of the bands applied to the paper. It is then possible to determine whether the cigarette formed from the banded wrapper will tend to exhibit acceptable reduced IP and freeburn characteristics.

The present invention may be used in any step of the cigarette paper manufacturing process at or after the point at which the bands have been applied to the paper. For example, if the bands are applied to the web on the paper making machine, the system of the present invention can be incorporated into the paper making machine to examine the web at or downstream the point where the bands are applied. Alternatively, if the bands are subsequently applied on a paper printing machine, the system of the present invention can be incorporated into the paper printing machine to examine the web at or downstream the point where the bands are applied. In addition, the system of the present invention can be incorporated in any other downstream system or machine involved in the cigarette paper manufacturing process, such as a paper slitter machine or a bobbin rewinder machine.

One aspect of the present invention relates to an image capture module comprising a trigger device, an illuminating device and an image capturing device disposed along the paper web path at or downstream the point where the bands are applied. The image capture module is adapted to obtain an image of at least one transverse banded region on the reduced IP paper. The widths of the transverse banded regions are measured and analyzed to determine whether a population of cigarettes formed with the paper will exhibit acceptable reduced IP and freeburn characteristics.

Another aspect of the present invention relates to a method of measuring the widths of the transverse banded regions on a bobbin or web of reduced IP paper. Such a method comprises determining the gray-scale values of each pixel of a captured image of the paper, converting the matrix of gray-scale values to a one-dimensional projection and filtering any noise or interference contributed by features of the paper other than the banded regions.

Another aspect of the present invention relates to the analysis of the band width data of a bobbin or web of reduced IP paper to determine whether a population of cigarettes formed with the paper will tend to exhibit acceptable reduced IP and freeburn characteristics. Such an analysis involves generating a target band width range for cigarette paper having acceptable reduced IP and freeburn characteristics. The band width data of a specific bobbin or web of cigarette paper may then be compared to the target band width range to determine whether the cigarette paper will tend to exhibit acceptable reduced IP and freeburn characteristics.

Other and further aspects of the invention will become apparent from the following detailed description with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A is a perspective view of an optical data capture and analysis system on a paper printing machine according to an embodiment of the invention;

FIG. 4A is a schematic top view of the image capture components illustrated in FIG. 3B;

FIG. 4B is a schematic side cross-sectional view of the illuminating device shown in FIG. 3B;

DETAILED DESCRIPTION OF THE PREFERRED EMBODIMENTS

Figure 1:
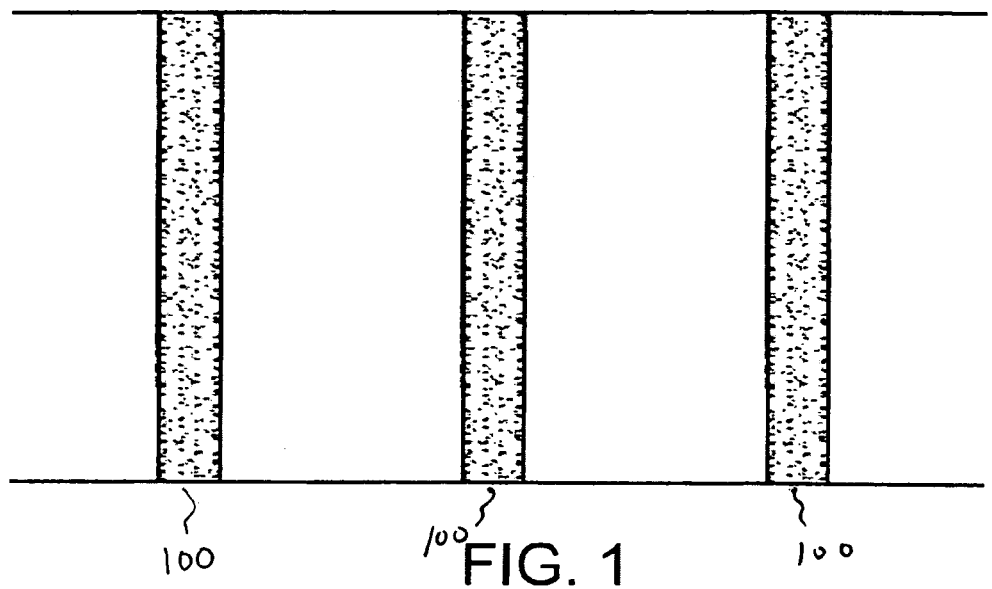
FIG. 1 is a plan view of a bobbin of cigarette paper having circumferential banded regions, prior to being slitted into wrappers that surround tobacco columns to form reduced IP cigarettes.
Figure 2:
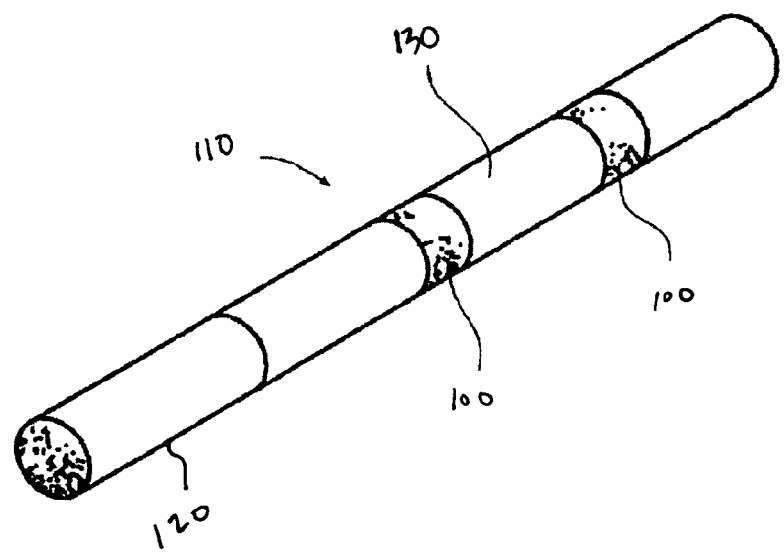
FIG. 2 is a perspective view of an exemplary cigarette having a wrapper containing circumferential banded regions.

The present invention will now be described with reference to the drawings, where like numerals refer to like elements throughout. It will be understood that the drawings are for the purpose of illustrating preferred embodiments of the invention and are not intended to limit the invention thereto. It will also be understood that other advancing embodiments may be utilized, and structural and functional modifications may be made, without departing from the scope of the present invention.

The invention provides a method and system for capturing and analyzing image data associated with the application of material to discrete regions of paper used to make cigarette wrappers. The inventive method and system also encompasses determining product performance characteristics based on the data captured and analyzed.

Image Data Capture

FIG. 3A shows a preferred embodiment of the image data capture components of the present invention incorporated on a paper printing machine where paper web 210 is moving in the direction of arrow 150. In this preferred embodiment, an image data capture module 225 is coupled to a cross bar 300 that spans the width of paper web 210. As shown here, the image data capture module 225 is coupled on the paper printing machine downstream the location where the gravure roll (not shown) prints banded regions 100 on the paper web 210. The image data capture module 225 may be slidably coupled on cross bar 300 to allow the image data capture module to be positioned at any location along the width of the paper web 210.

The image data capture module 225 includes a trigger device 230, an illuminating device 240 and an image capturing device 235. As shown in FIG. 3A, trigger device 230 is located upstream paper illuminating device 240 and image capturing device 230 relative to the direction of movement of paper web 210. In this implementation, the trigger device 230 is a fiber-optic sensor that is adapted to detect banded regions on the moving paper web 210. The trigger device 230 communicates with paper illuminating device 240 and image capturing device 235 and initiates the capture of some or all of the banded regions on moving paper web 210. It will be understood that trigger device 230 may be configured to communicate with illuminating device 240 and image capturing device 235 using any conventional wired or wireless communication system. Depending on the speed at which the paper web 210 moves, trigger device 230 may be adapted to initiate the capture of an image of each detected banded region on the paper web 210 or periodic samples of banded regions on the paper web 210 (e.g., every third banded region).

A more detailed description of the present invention will now be provided with reference to an embodiment of the image data capture module 225 incorporated in a cigarette paper bobbin rewinder machine 200 as illustrated in FIGS. 3B-5. It will be understood that, although the invention is discussed and illustrated in connection with a bobbin rewinder machine 200, the invention may be adapted for use in machines having different operating speeds. Accordingly, the present invention may be adapted for use in both the high speed operation of a paper making machine or paper printing machine or the lower speed operation of a bobbin rewinder machine.

Figure 3B:
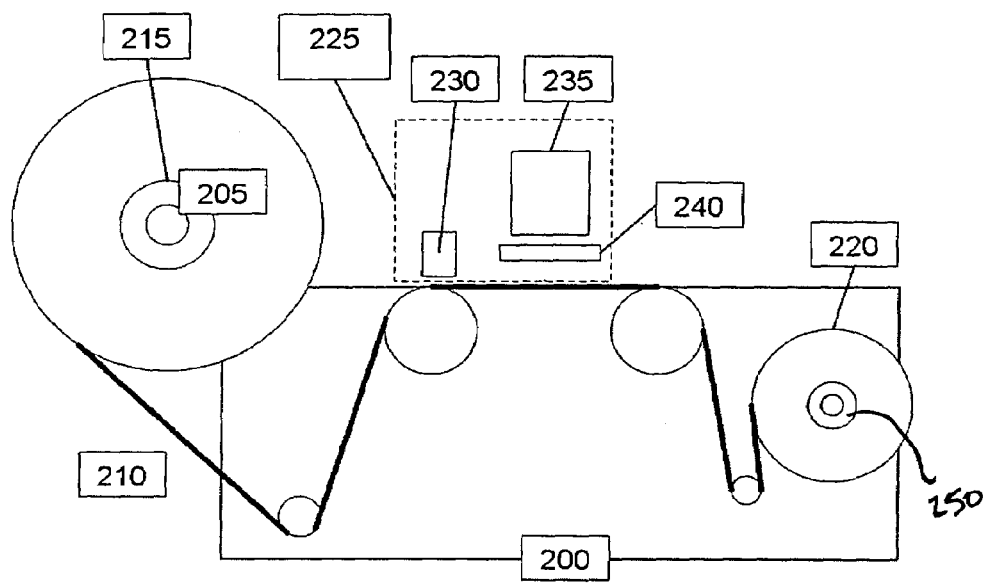
FIG. 3B is a schematic side view of an optical data capture and analysis system on a bobbin rewinder machine according to an embodiment of the invention.

As shown in FIG. 3B, a bobbin of reduced IP cigarette paper 205 is removably engaged on a spindle 215 of the rewinder machine 200. The paper 210 is routed from bobbin 205 through a series of tensioning rollers to a rewind bobbin 220, which is coupled to a rewind spindle assembly 250. The rewind spindle assembly is driven by a drive system for unwinding the paper 210 from bobbin 205 to rewind bobbin 220.

As further shown in FIG. 3B, an image data capture module 225 is positioned on the rewinder machine along the paper path between bobbin 205 and rewind bobbin 220. Similar to the system shown in FIG. 3A, the image data capture module 225 includes a trigger device 230, an illuminating device 240 and an image capturing device 235.

The trigger device 230 may be an encoder device which conducts coarse detection analysis. By way of example, trigger device 230 may be a fiber-optic LED encoder sensor adapted to perform coarse reflectivity analysis such as the model FS-V21RP fiber-optic sensor and the model FU-10 fiber-optic probe, both manufactured by Keyence. It will be understood, however, that the trigger device may comprise other optical and non-optical based devices, such as NIR absorption devices or ultrasonic transmission devices or translucent-based optical devices.

In operation, the fiber-optic sensor emits an amplified LED light beam onto the surface of moving paper web 210 and measures the amount of the light reflected back. The sensor compares the amount of the reflected light with a threshold value to determine whether the amount of reflected light is indicative of a banded region or an unbanded region on the moving paper web. Accordingly, the sensor is able to detect the banded regions as the paper web 210 moves through the processing stream. Upon detecting a banded region, trigger device 230 transmits at least one signal to initiate (1) illuminating device 240 to emit a strobe light to illuminate a portion of the moving paper web containing at least one banded region and (2) image capturing device 235 to capture an image of an illuminated portion of the moving paper web containing at least one banded region. It will be understood that trigger device 230 may transmit the initiation signals directly to illuminating device 240 and image capturing device 235 to actuate the devices to capture an illuminated image of a portion of the moving web containing at least one banded region. Alternatively, the trigger device may transmit the initiation signals to one or more controller, control interface and/or processor which, in turn, communicate with and actuate the illuminating device and image capturing device.

Figure 6A:
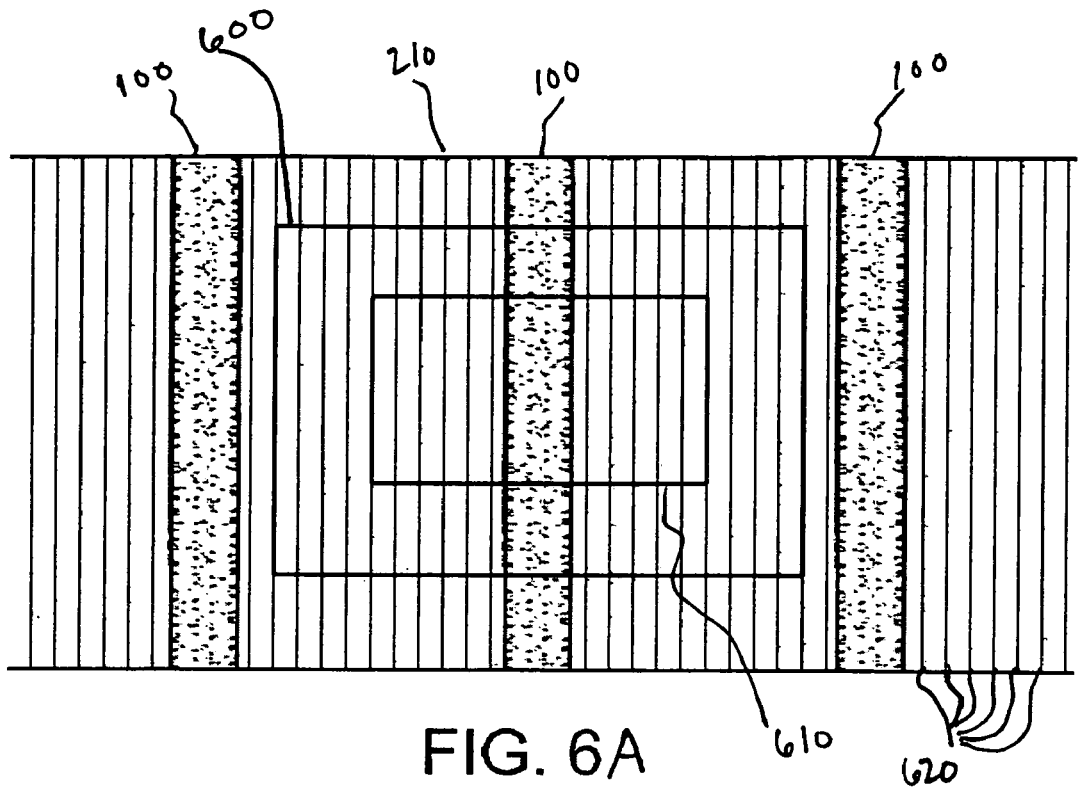
FIG. 6A illustrates a detailed illustration of an image data capture area according to an embodiment of the invention.

It has been found that the measured dimensions of a banded region may vary slightly depending on the position of the banded region within the captured image. Accordingly, applicants have found that the most accurate measure of the banded regions can be obtained when the banded regions captured in each successive image are consistently positioned at generally the same location within the captured images. For example, with regard to the measure of the width of a single banded region within an image, an accurate measure of the banded regions in successive images may be achieved by positioning the measured band of each image at the longitudinal centerpoint of the captured image as shown in FIG. 6A. To this end, trigger device 230 is preferably adapted to initiate image capturing device 235 and illuminating device 240 so that each measured banded region is centered longitudinally within the captured image. It has been determined that this can be achieved by positioning the trigger device 230 a distance from the center of the captured image equal to an integral multiple of the distance between the centers of adjacent banded regions on the paper. With regard to the measure of multiple banded regions within each captured image of the moving web, it has similarly been found that an accurate measure of the banded regions can be achieved by consistently positioning the measured banded regions at or about the same locations for each successive captured image.

FIG. 4A illustrates a top view of an embodiment of image data capture module 225 with regard to a web moving in the direction of arrow 405. As discussed above, trigger device 230 (e.g., fiber-optic LED encoder sensor) detects the transverse banded regions as they pass within a detection zone. Trigger device 230 is disposed upstream of and is in communication with illuminating device 240 and the image capturing device 235. In this embodiment, illuminating device 240 has an annular-shaped housing with a single row of LEDs mounted adjacent each other. The annular-shaped illuminating device may comprise any suitable LED strobe light such as the model LDR-146LA-1-BL manufactured by CCS. When trigger device 230 detects a banded region on the moving paper web 210, it generates a signal that initiates illuminating device 240 to illuminate a portion of the moving paper web 210 containing at least one transverse banded region when it is in the field of view of the image capturing device 235. Trigger device 230 signal also initiates the image capturing device 235 to capture an image of the illuminated portion of the moving paper web 210 containing the banded region. As provided above, trigger device 230 can be configured to initiate operation of illuminating device 240 and image capturing device 235 to illuminate and capture the image of every banded region or periodic banded regions. For example, in one implementation the trigger device 230 may be configured to periodically initiate image capturing device 235 and illuminating device 240 to capture images of every third banded region of the paper web 210. In this implementation, the system may be configured to include a control interface such as a plc controller to actuate the illumination device 240 and image capturing device 235 to capture every third banded region on moving paper web 210.

It will be understood that the banded regions captured in the image of the portion of the moving web of paper may or may not include the detected banded region which causes the trigger device to initiate the illumination and acquisition of the image. It will also be understood that trigger device 230 may be located upstream or downstream illuminating device 240 and image capturing device 235. According to the arrangement where trigger device 230 is located downstream illuminating device 240 and image capturing device 235, the trigger device may be configured to initiate the acquisition of an upstream banded region by taking into account the known spacing between adjacent transverse banded regions and the speed of at which the paper web 210 is traveling through the machine.

FIG. 4B illustrates a cross-sectional side view of annular-shaped illuminating device 240. It will be understood that LEDs 245 may be adjusted to emit the light at a range of angles of incidence relative to moving paper web 210. For example, as shown in FIG. 4B, LEDs 245 may be inclined downwardly toward moving paper web 210 to provide an angle of incidence θ of approximately 45 degrees. It will be understood that a 0 degree angle of incidence for this system corresponds to LEDs which are not downwardly inclined as show in FIG. 4B, but which are aligned to emit light beams in a direction parallel to moving paper web.

It will be understood that the contrast between the banded and unbanded regions in the illuminated captured image of the moving paper web 210 may be optimized by varying the angle of incidence of the light emitted from LEDs 245. For example, it has been found that with regard to a paper web having banded regions formed from starch-based material, the contrast between the banded and unbanded regions in the captured image may be optimized when the angle of incidence of the light emitted from the LEDS is approximately 0 degrees. With reference to the annular illuminating device 240 shown in FIG. 4B, a 0 degree angle of incidence may be achieved by aligning the LEDs to face inwardly and emit light in a plane parallel to the plane defined by moving paper web 210.

It has also been found that the contrast between the banded and unbanded regions in the captured image of the moving paper web may be optimized by adjusting the frequency of the light emitted from the LEDs. For example, with regard to a paper web having banded regions formed from starch-based material, the contrast between the banded and unbanded regions in the captured image may be optimized by emitting light from the LEDs at a frequency of about 475 nm.

Additional variables that can be adjusted to optimize the contrast between banded and non-banded regions of a captured image of a paper web include: (1) the distance between the illuminating device and the paper web; (2) the distance of between the image capturing device (e.g., camera) and the paper web; (3) the depth of focus and the focal length of the lens system associated with the image capturing device; (4) the aperture size of the image capturing device; and (5) the frequency at which the illuminating device is triggered. With regard to starch-based band material, it has been found that minimizing the distance between the illuminating device and the paper web results in captured image data having a high degree of contrast between banded and non-banded regions. It will be understood that each of these operating parameters may be tuned to achieve maximum contrast between the banded and non-banded regions of paper having bands made from different band material.

Preferably, image capturing device 235 comprises a high resolution camera suitable for high speed image processing such as the XC-HR50 monochrome CCD camera manufactured by Sony. Image capturing device 235 is initiated by trigger device 230 to capture an illuminated image of a portion of moving paper web 210 containing a banded region. As described in more detail below, information from the captured images are transferred to a processing unit (not shown) for analysis.

It will be understood that the system of the present invention may include a plurality of cameras transversely disposed at various positions along the moving web to obtain a broader sampling of image data of the banded regions. Alternatively, the system may include a single camera which is adapted to move transversely along the moving web and capture images of different transverse portions of the web.

Figure 5:
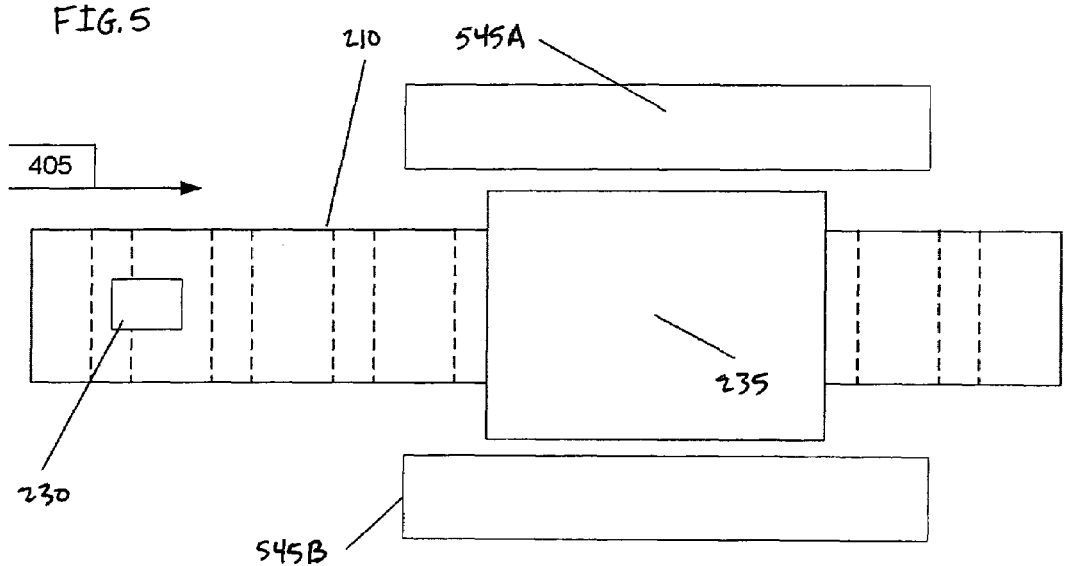
FIG. 5 is a schematic top view of an alternate embodiment of the image capture components of the present invention.

FIG. 5 illustrates an alternate embodiment of the invention on a bobbin rewinder machine where the illuminating device is configured as two strips of LEDs 545A and 545B disposed parallel to either side of the web 215. The implementation illustrated in FIG. 5 includes trigger device 230, which controls image capturing device 235 and both illuminating devices 545A and 545B. It will be understood that illuminating devices 545A, 545B provide a light source for illuminating an image capture area on web 210. When illuminating devices 545A and 545B are initiated in coordination with image capturing device 235, it is possible to obtain images with optimal contrast between the banded and non-banded regions for subsequent analysis. As with the embodiment illustrated in FIG. 4A, this arrangement can also be used with a paper making machine or a paper printing machine.

Analysis of Captured Image Data

As paper web 210 is transferred from bobbin 205 to rewind bobbin 220 on rewinder machine 200, the system captures illuminated images of portions of the paper web containing the discrete banded regions. Applicants have found that there is a correlation between the widths of the banded regions on the paper 210 and the IP and freeburn properties of cigarettes having wrappers formed from the paper 210. According to the present invention, information from the captured images is analyzed to determine the widths of the banded regions of the paper. By way of example, the cigarette paper may have banded regions comprising transverse bands of material having a target width of 6 millimeters. The analysis of image data focuses on discerning the transition areas between banded and non-banded regions in order to calculate the width of each of the measured banded regions of a bobbin of paper.

Figure 6B:
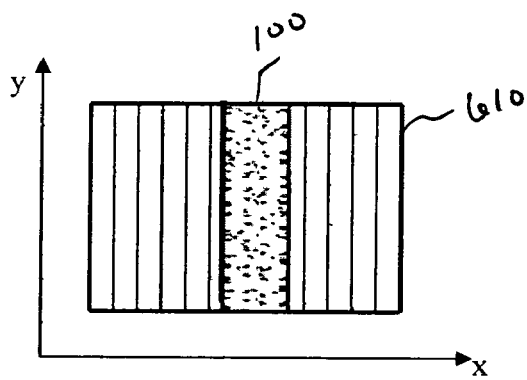
FIG. 6B is a detailed illustration of an image data capture area according to an embodiment of the invention.

FIG. 6A illustrates an example of a captured image 600 of paper web 210 having transverse banded regions 100 taken by image capturing device 235 (shown in FIGS. 3 and 4A). As shown in FIG. 6A, only a portion (rectangular area 610 shown in FIGS. 6A and 6B) of the entire image taken by image capturing device 235 is analyzed. It will be understood that during the normal course of operation the paper 210 may inadvertently move relative to the image capturing device 235. By analyzing only the rectangular area in the center portion 610 of the captured image 600, the system will still obtain usable information even if paper web 210 is momentarily displaced laterally relative to the image capturing device 235 on the bobbin rewinder machine 200.

Figure 7:
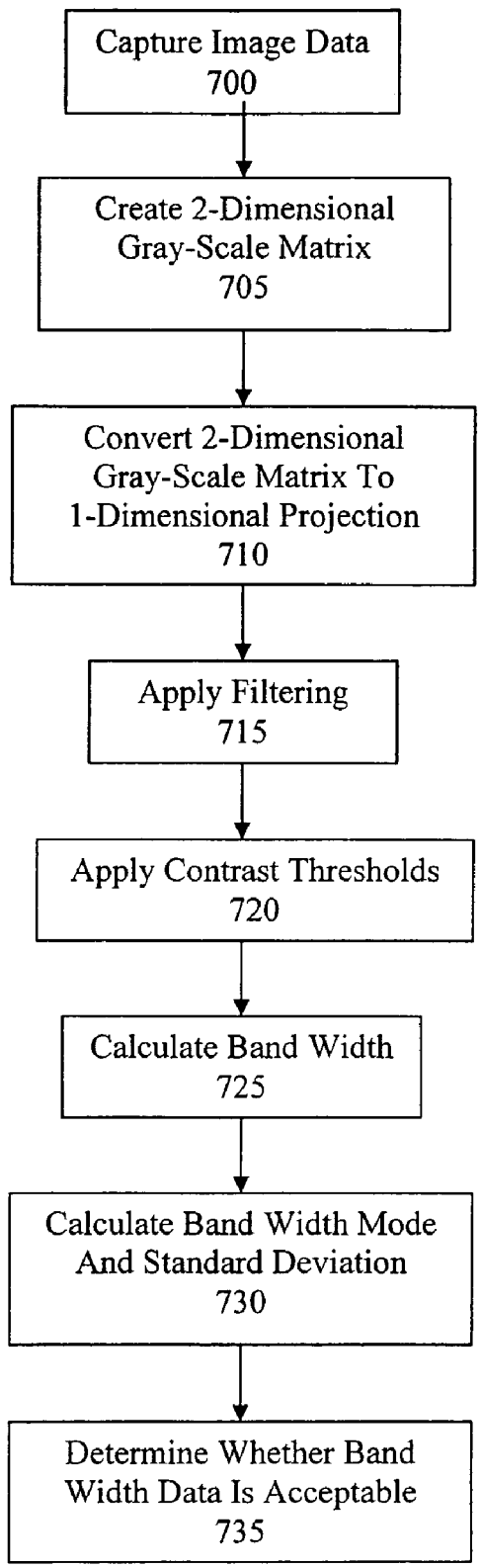
FIG. 7 is a flow diagram associated with an image processing method for analyzing the captured image data.

FIG. 7 illustrates a flow diagram of the captured image data analysis process. The process starts in step 700 with capturing the image 600 of the paper 210, as described above with reference to FIGS. 3-6B. Once an image 600 is captured, the system creates a gray-scale matrix in step 705 by assigning gray-scale values for each pixel in the image. In step 710, the two-dimensional gray scale matrix is converted to a one-dimensional projection in the x-direction. In one implementation this can be achieved by calculating the sum of all of the gray scale values for the pixels in each column of pixels. Alternatively, the one-dimensional projection may be calculated by calculating the average gray scale value for all of the pixels in each column of pixels. For future reference, an x-y coordinate system has been superimposed on the image analysis area shown in FIG. 6B. The y-coordinate corresponds to the direction along the lateral width of the paper. The x-coordinate corresponds to the direction of travel of the paper moving through the machine, i.e., the longitudinal direction of the paper.

In step 715, the one-dimensional projection data is filtered to decrease the effect of noise captured on the image. In step 720, predetermined threshold parameters are applied to the projection data to identify the leading and trailing edges of the banded region. Once the locations of the edges of the banded region are determined, the band width is calculated in step 725. In step 730, all of the measured band widths are compiled and the mode and standard deviation are determined. Finally, in step 735 the mode and standard deviation data of the analyzed paper are compared with predetermined mode and standard deviation data for acceptable reduced IP paper to determine whether the analyzed paper meets specifications. Additional detail regarding the analysis process will be discussed below.

Step 705 involves generating a gray-scale matrix corresponding to the captured image data. Individual pixel gray-scale values are generated for each of the pixels of the image in the inspection area 610. These individual pixel gray-scale numbers produce a matrix of gray-scale values corresponding to each pixel position. When illuminated by illuminating device 240, the banded region 100 has an overall darker contrast than the base cigarette paper. The gray-scale is chosen such that the range of values spans 0-255, with 0 corresponding to black and 255 to white. Alternately, these values may be inverted with 0 corresponding to white and 255 corresponding to black.

In step 710, the two-dimensional gray-scale matrix is converted to a one-dimensional projection by summing the gray-scale values of all of the pixels in each of the columns of pixels. The top graph in FIG. 8 shows a plot of projection data along the x-axis.

Typically, base cigarette paper includes a series of "vergé" lines 620 printed on the paper in a lateral direction. These vergé lines are aesthetic in nature and typically appear at equally spaced intervals of about 1 mm. As shown in FIG. 6A, these vergé lines, like the banded regions, have a dark contrast on the captured image when illuminated by illuminating device 240. Accordingly, the vergé lines also are assigned gray-scale values similar to the values of the banded region and, therefore, create interference or noise in the projection data. As described below, the system of the present invention is adapted to filter out the effect of the vergé lines on the projection data.

In step 715, the projection data is filtered to eliminate or minimize the interference effect of the vergé lines. In one implementation of the present invention, the filtering technique is accomplished by calculating a derivative of the projection data with respect to the x-axis. A smoothing parameter, referred to as the filter half size pixel, may also be applied to the derivative of the projection data to better distinguish the change in contrast between the unbanded portions of the paper web and the leading and trailing edges of the banded regions. The bottom graph in FIG. 8 illustrates a plot of the filtered projection data for a captured image of the cigarette paper. The degree to which the projection data is filtered can be varied by changing the filter half size pixel value.

Figure 8:
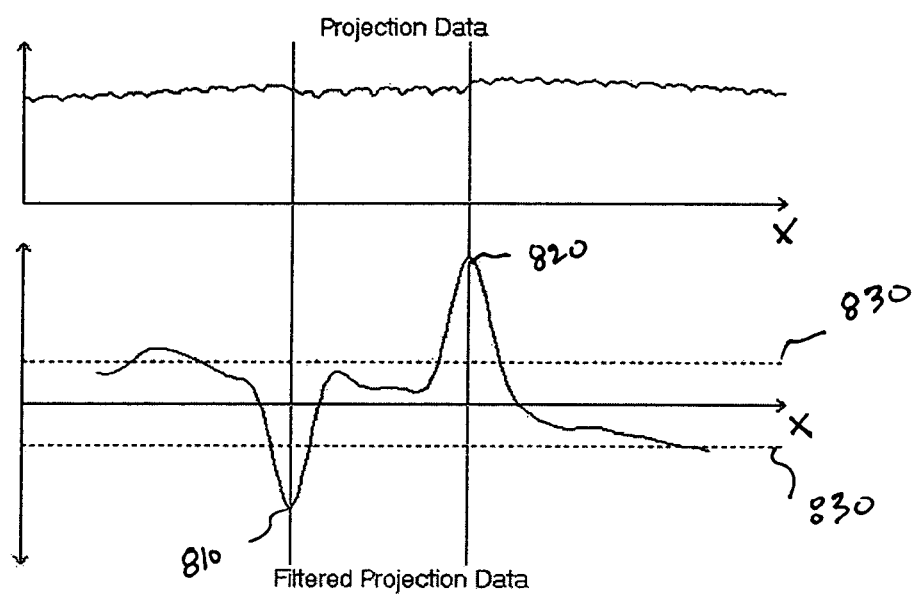
FIG. 8 illustrates two waveforms corresponding to data derived from the image in the image data analysis area shown in FIG. 6B.

As shown in the bottom graph in FIG. 8, the filtered projection data contains minima and maxima peaks 810, 820 corresponding to the leading and trailing edges of the banded region. The minima and maxima peaks represent distinct changes in the contrast between the lighter unbanded regions and the darker banded regions as shown in the captured image of the cigarette paper. The smaller peaks or noise shown in this graph represent the less significant changes in contrast created by the vergé lines.

It an alternative implementation, the filtering step may be carried out by performing a Fourier transform on the band width projection data to eliminate or minimize the noise or interference attributable to the vergé lines.

A contrast threshold is selected to distinguish and isolate the minima and maxima peaks 810, 820 corresponding to the leading and trailing edges of the banded region from the noise in the graph of the filtered projection data. The contrast threshold parameter is a predetermined value based on an empirical analysis of filtered projection data for paper having banded regions treated with a particular material. Accordingly, the contrast threshold for webs of paper having banded regions formed from different material or amounts of material may vary. This parameter sets the actual thresholds for conducting banded region edge determinations within the captured image data. In FIG. 8, the contrast threshold is illustrated as the two horizontal dashed lines 830 in the filtered projection data curve. The minima and maxima peaks 810, 820 are defined as the peaks extending beyond the contrast threshold 830. The width of the banded region is calculated by taking the difference in the two x coordinates of the leading and trailing edges of the banded regions as defined by the minima and maxima peaks 810, 820. The widths of all of the measured banded regions on the bobbin of paper are compiled and the mode and standard deviation of all the band widths are determined.

Predictive Analysis

Applicants have found that there is a direct correlation between the widths of the banded regions of the paper and the reduced IP and freeburn characteristics of the cigarettes made with the paper. More specifically, applicants have conducted empirical analysis to confirm that the reduced IP and freeburn characteristics of a population of cigarettes may be predicted based on the mode and standard deviation of the band width distributions on the cigarette paper. It will be understood that the target mode and standard deviation of the band widths for a population of cigarettes having acceptable reduced IP and freeburn characteristics will depend on various factors, including the basis weight of the paper, the composition of the banded material and the method of application of the banded material to the paper.

Figure 9:
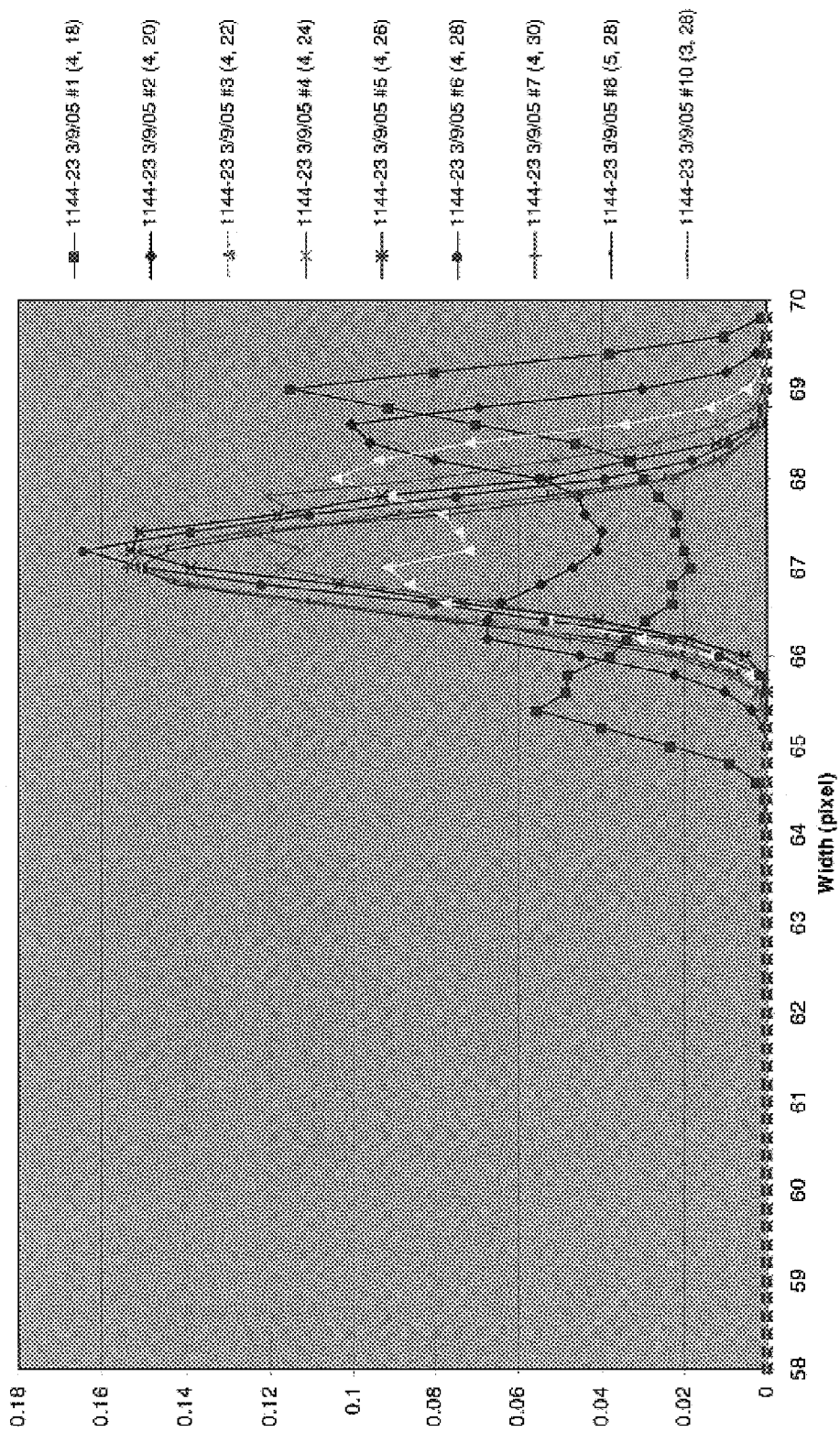
FIG. 9 illustrates the analysis used to select the optimal software parameters to produce a normal distribution of band width data for reduced IP paper.

FIG. 9 contains a series of plots of band width distribution data based on the application of different contrast threshold values and filter half size pixel values for a population of cigarettes having acceptable reduced IP and freeburn characteristics. The band width data was obtained by measuring 5000 consecutive bands on a bobbin of reduced IP cigarette paper. As shown in FIG. 9, the contrast threshold and filter half size pixel parameters must be selected to obtain a normal distribution of band width measurements. In this example, a normal distribution is obtained by selecting a contrast threshold value of 4 and a filter half size pixel value of 28.

The normal distribution of band width measurements shown in FIG. 9 can be used as a standard for comparison with analyzed bobbins of reduced IP paper. It has been found that if the band width data of a bobbin of reduced IP paper deviates from the standard band width data, the population of cigarettes formed from the bobbin of reduced IP paper will exhibit unacceptable IP and/or freeburn characteristics. For example, a population of cigarettes having a band width mode less than the standard band width mode will tend to exhibit acceptable freeburn characteristics, but unacceptable reduced IP characteristics. Similarly, a population of cigarettes having a band width mode greater than the standard band width mode will tend to exhibit acceptable reduced IP characteristics, but unacceptable freeburn characteristics. In addition, a bobbin of paper having a band width standard deviation greater than that of the standard paper will tend to exhibit unacceptable freeburn and reduced IP characteristics.

Image Data Capture, Analysis, and Prediction (IDCAP) Controller

Figure 10:
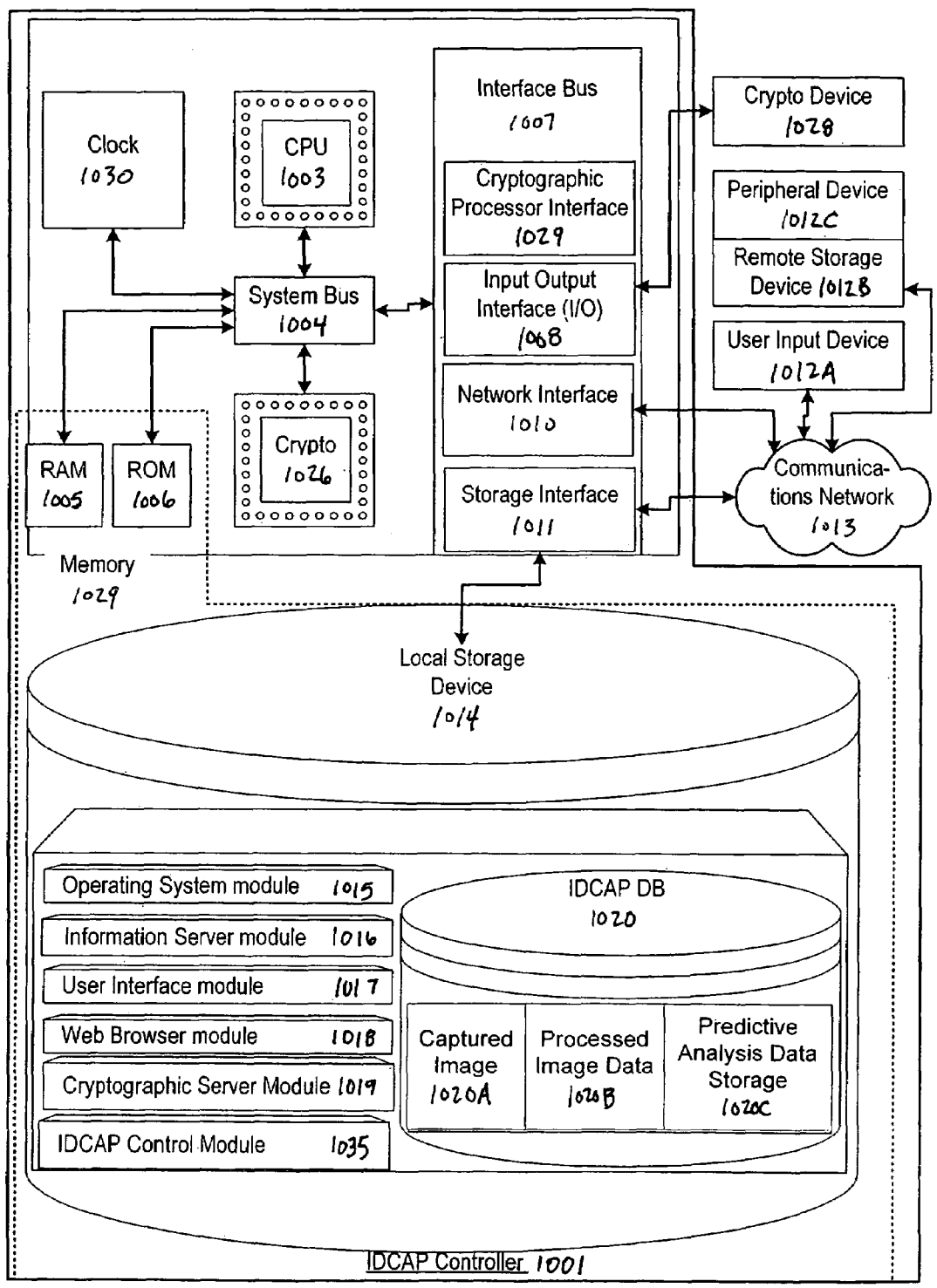
FIG. 10 is a diagram of hardware components/software modules associated with an Image Data Capture, Analysis, and Prediction (IDCAP) controller.

FIG. 10 is of a block diagram illustrating an embodiment of an Image Data Capture, Analysis and Prediction (IDCAP) controller. In this embodiment, the IDCAP controller 801 may serve to process, store, search, serve, identify, instruct, generate, match, and/or update securities related data.

In one embodiment, the IDCAP controller 1001 may be connected to and/or communicate with entities such as, but not limited to: one or more users from user input devices 1012A; remote storage devices 1012B; peripheral devices 1012C; and/or a communications network 1013. The IDCAP controller 1001 may even be connected to and/or communicate with a cryptographic processor device 1028.

A IDCAP controller 1001 may be based on common computer systems that may comprise, but are not limited to, components such as: a computer systemization connected to memory 1029.

Computer Systemization

A computer systemization may comprise a clock 1030, central processing unit (CPU) 1003, a read only memory (ROM) 1006, a random access memory (RAM) 1005, and/or an interface bus 1007, and most frequently, although not necessarily, are all interconnected and/or communicating through a system bus 1004. Optionally, the computer systemization may be connected to an internal power source. Optionally, a cryptographic processor 1026 may be connected to the system bus 1004. The system clock 1030 typically has a crystal oscillator and provides a base signal. The clock 1030 is typically coupled to the system bus 1004 and various clock multipliers that will increase or decrease the base operating frequency for other components interconnected in the computer systemization.

The clock 1030 and various components in a computer systemization drive signals embodying information throughout the system. Such transmission and reception of signals embodying information throughout a computer systemization may be commonly referred to as communications. These communicative signals may further be transmitted, received, and the causes of return and/or reply signal communications beyond the instant computer systemization to: communications networks, input devices, other computer systemizations, peripheral devices and/or the like. Of course, any of the above components may be connected directly to one another, connected to the CPU 1003 and/or organized in numerous variations employed as exemplified by various computer systems.

The CPU 1003 comprises at least one high-speed data processor adequate to execute program modules for executing user and/or system-generated requests. The CPU may be a microprocessor such as AMD's Athalon, Duron and/or Opteron; IBM and/or Motorola's PowerPC; Intel's Celeron, Itanium, Pentium, Xeon, and/or XScale; and/or the like processor(s). The CPU interacts with memory through signal passing through conductive conduits to execute stored program code according to conventional data processing techniques. Such signal passing facilitates communication within the IDCAP controller 1001 and beyond through various interfaces. Should processing requirements dictate a greater amount speed, mainframe and super computer architectures may similarly be employed. Alternatively, should deployment requirements dictate greater portability, smaller Personal Digital Assistants (PDAs) may be employed.

Power Source

The power source may be of any standard form for powering small electronic circuit board devices such as the following power cells: alkaline, lithium hydride, lithium ion, nickel cadmium, solar cells and/or the like. Other types of AC or DC power sources may be used as well. In the case of solar cells, in one embodiment, the case provides an aperture through which the solar cell may capture photonic energy. The power cell is connected to at least one of the interconnected subsequent components of the IDCAP controller 1001 thereby providing an electric current to all subsequent components. In one example, the power source is connected to the system bus component 1004. In an alternative embodiment, an outside power source is provided through a connection across the I/O 808 interface. For example, a USB and/or IEEE 1394 connection carries both data and power across the connection and is therefore a suitable source of power.

Interface Adapters

Interface bus(ses) 1007 may accept, connect, and/or communicate to a number of interface adapters, conventionally although not necessarily in the form of adapter cards, such as but not limited to: input output interfaces (I/O) 1008, storage interface 1011, network interface 1010, and/or the like. Optionally, cryptographic processor interfaces 1029 similarly may be connected to the interface bus. The interface bus provides for the communications of interface adapters with one another as well as with other components of the computer systemization. Interface adapters are adapted for a compatible interface bus. Interface adapters conventionally connect to the interface bus via a slot architecture. Conventional slot architectures may be employed, such as, but not limited to: Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and/or the like.

Storage interfaces 1011 may accept, communicate, and/or connect to a number of storage devices such as, but not limited to: storage devices 1014, removable disc devices, and/or the like. Storage interfaces may employ connection protocols such as, but not limited to: (Ultra) (Serial) Advanced Technology Attachment (Packet Interface) ((Ultra) (Serial) ATA(PI)), (Enhanced) Integrated Drive Electronics ((E)IDE), Institute of Electrical and Electronics Engineers (IEEE) 1394, fiber channel, Small Computer Systems Interface (SCSI), Universal Serial Bus (USB), and/or the like.

Network interfaces 1010 may accept, communicate, and/or connect to a communications network 813. Network interfaces may employ connection protocols such as, but not limited to: direct connect, Ethernet (thick, thin, twisted pair 10/100/1000 Base T, and/or the like), Token Ring, wireless connection such as IEEE 802.11a-x, and/or the like. A communications network may be any one and/or the combination of the following: a direct interconnection; the Internet; a Local Area Network (LAN); a Metropolitan Area Network (MAN); an Operating Missions as Nodes on the Internet (OMNI); a secured custom connection; a Wide Area Network (WAN); a wireless network (e.g., employing protocols such as, but not limited to a Wireless Application Protocol (WAP), I-mode, and/or the like); and/or the like. A network interface may be regarded as a specialized form of an input output interface. Further, multiple network interfaces 1010 may be used to engage with various communications network types 1013. For example, multiple network interfaces may be employed to allow for the communication over broadcast, multicast, and/or unicast networks.

Input Output interfaces (I/O) 1008 may accept, communicate, and/or connect to user input devices 1012A, remote storage device 1012B, peripheral devices 1012C, cryptographic processor 1026, and/or the like. I/O may employ connection protocols such as, but not limited to: Apple Desktop Bus (ADB); Apple Desktop Connector (ADC); audio: analog, digital, monaural, RCA, stereo, and/or the like; IEEE 1394a-b; infrared; joystick; keyboard; midi; optical; PC AT; PS/2; parallel; radio; serial; USB; video interface: BNC, composite, digital, Digital Visual Interface (DVI), RCA, S-Video, VGA, and/or the like; wireless; and/or the like. A common output device is a video display, which typically comprises a Cathode Ray Tube (CRT) or Liquid Crystal Display (LCD) based monitor with an interface (e.g., DVI circuitry and cable) that accepts signals from a video interface. The video interface composites information generated by a computer systemization and generates video signals based on the composite information in a video memory frame. Typically, the video interface provides the composited video information through a video connection interface that accepts a video display interface (e.g., a DVI connector accepting a DVI display cable).

User input devices 1012A may be card readers, dongles, finger print readers, gloves, graphics tablets, joysticks, keyboards, mouse (mice), trackballs, trackpads, retina readers, and/or the like.

Peripheral devices 1012C may be connected and/or communicate to I/O and/or other facilities of the like such as network interfaces, storage interfaces, and/or the like. Peripheral devices may be audio devices, cameras, dongles (e.g., for copy protection, ensuring secure transactions with a digital signature, and/or the like), external processors (for added functionality), goggles, microphones, monitors, network interfaces, printers, scanners, storage devices, video devices, visors, and/or the like.

It should be noted that although user input devices and peripheral devices may be employed, the IDCAP controller 801 may be embodied as an embedded, dedicated, and/or headless device, wherein access would be provided over a network interface connection.

Cryptographic units such as, but not limited to, microcontrollers, processors 1026, interfaces 1029, and/or devices 1028 may be attached, and/or communicate with the IDCAP controller 1001. A MC68HC16 microcontroller, commonly manufactured by Motorola Inc., may be used for and/or within cryptographic units. Equivalent microcontrollers and/or processors may also be used. The MC68HC16 microcontroller utilizes a 16-bit multiply-and-accumulate instruction in the 16 MHz configuration and requires less than one second to perform a 512-bit RSA private key operation. Cryptographic units support the authentication of communications from interacting agents, as well as allowing for anonymous transactions. Cryptographic units may also be configured as part of CPU. Other commercially available specialized cryptographic processors include VLSI Technology's 33 MHz 6868 or Semaphore Communications' 40 MHz Roadrunner 184.

Memory

Generally, any mechanization and/or embodiment allowing a processor to affect the storage and/or retrieval of information is regarded as memory 1023. However, memory is a fungible technology and resource, thus, any number of memory embodiments may be employed in lieu of or in concert with one another. It is to be understood that a IDCAP controller 1001 and/or a computer systemization may employ various forms of memory 1023. For example, a computer systemization may be configured wherein the functionality of on-chip CPU memory (e.g., registers), RAM, ROM, and any other storage devices are provided by a paper punch tape or paper punch card mechanism; of course such an embodiment would result in an extremely slow rate of operation. In a typical configuration, 1023 will include ROM 1006, RAM 1005, and a storage device 1014. A storage device 1014 may be any conventional computer system storage. Storage devices may include a drum; a (fixed and/or removable) magnetic disk drive; a magneto-optical drive; an optical drive (i.e., CD ROM/RAM/Recordable (R), ReWritable (RW), DVD R/RW, etc.); and/or other devices of the like. Thus, a computer systemization generally requires and makes use of memory.

Module Collection

The memory 1023 may contain a collection of program and/or database modules and/or data such as, but not limited to: operating system modules 1015 (administration control module); information server module(s) 1016 (information server); user interface module(s) 1017 (user interface); Web browser module(s) 1018 (Web browser); database(s) 1019; cryptographic server module(s) 1020 (cryptographic server); IDCAP controller module(s) 1035; and/or the like (i.e., collectively a module collection). These modules may be stored and accessed from the storage devices and/or from storage devices accessible through an interface bus. Although non-conventional software modules such as those in the module collection, typically, are stored in a local storage device 1014, they may also be loaded and/or stored in memory such as: peripheral devices, RAM, remote storage facilities through a communications network, ROM, various forms of memory and/or the like.

Operating System

The operating system module 1015 is executable program code facilitating the operation of a IDCAP controller 1001, including the distributor and ad arbitrator modules discussed above. Typically, the operating system facilitates access of I/O, network interfaces, peripheral devices, storage devices and/or the like. The operating system may be a highly fault tolerant, scalable, and secure system such as Apple Macintosh OS X (Server), AT&T Plan 9, Be OS, Linux, Unix and/or the like operating systems. However, more limited and/or less secure operating systems also may be employed such as Apple Macintosh OS, Microsoft DOS, Palm OS, Windows 2000/2003/3.1/95/98/CE/Millenium/NT/XP (Server), and/or the like. An operating system may communicate to and/or with other modules in a module collection, including itself, and/or the like. Most frequently, the operating system communicates with other program modules, user interfaces and/or the like. For example, the operating system may contain, communicate, generate, obtain and/or provide program module, system, user and/or data communications, requests and/or responses. The operating system, once executed by the CPU, may enable the interaction with communications networks, data, I/O, peripheral devices, program modules, memory, user input devices, and/or the like. The operating system may provide communications protocols that allow the IDCAP controller 1001 to communicate with other entities through a communications network 1013. Various communication protocols may be used by the IDCAP controller 1001 as a subcarrier transport mechanism for interaction, such as, but not limited to: multicast, TCP/IP, UDP, unicast and/or the like.

Information Server

An information server module 1016 is stored program code that is executed by the CPU. The information server may be a conventional Internet information server such as, but not limited to Apache Software Foundation's Apache, Microsoft's Internet Information Server and/or the like. The information server may allow for the execution of program modules through facilities such as Active Server Page (ASP), ActiveX, (ANSI) (Objective-) C (++), Common Gateway Interface (CGI) scripts, Java, JavaScript, Practical Extraction Report Language (PERL), Python, WebObjects, and/or the like. The information server may support secure communications protocols such as, but not limited to, File Transfer Protocol (FTP); HyperText Transfer Protocol (HTTP); Secure Hypertext Transfer Protocol (HTTPS), Secure Socket Layer (SSL), and/or the like. The information server provides results in the form of Web pages to Web browsers, and allows for the manipulated generation of the Web pages through interaction with other program modules. After a Domain Name System (DNS) resolution portion of an HTTP request is resolved to a particular information server, the information server resolves requests for information at specified locations on a IDCAP based on the remainder of the HTTP request. For example, a request such as http://123.124.125.126/myInformation.html might have the IP portion of the request "123.124.125.126" resolved by a DNS server to an information server at that IP address; that information server might in turn further parse the http request for the "/myInformation.html" portion of the request and resolve it to a location in memory containing the information "myInformation.html." Additionally, other information serving protocols may be employed across various ports, e.g., FTP communications across port 1021, and/or the like. An information server may communicate to and/or with other modules in a module collection, including itself, and/or facilities of the like. Most frequently, the information server communicates with the IDCAP database 1020, operating systems, other program modules, user interfaces, Web browsers, and/or the like.

Access to IDCAP database 1020 may be achieved through a number of database bridge mechanisms such as through scripting languages as enumerated below (e.g., CGI) and through inter-application communication channels as enumerated below (e.g., CORBA, WebObjects, etc.). Any data requests through a Web browser are parsed through the bridge mechanism into appropriate grammars as required by the IDCAP controller 1001. In one embodiment, the information server would provide a Web form accessible by a Web browser. Entries made into supplied fields in the Web form are tagged as having been entered into the particular fields, and parsed as such. The entered terms are then passed along with the field tags, which act to instruct the parser to generate queries directed to appropriate tables and/or fields. In one embodiment, the parser may generate queries in standard SQL by instantiating a search string with the proper join/select commands based on the tagged text entries, wherein the resulting command is provided over the bridge mechanism to the IDCAP controller 1001 as a query. Upon generating query results from the query, the results are passed over the bridge mechanism, and may be parsed for formatting and generation of a new results Web page by the bridge mechanism. Such a new results Web page is then provided to the information server, which may supply it to the requesting Web browser.

Also, an information server may contain, communicate, generate, obtain and/or provide program module, system, user and/or data communications, requests and/or responses.

User Interface

A user interface module 1017 is stored program code that is executed by the CPU. The user interface may be a conventional graphic user interface as provided by, with, and/or atop operating systems and/or operating environments such as Apple Macintosh OS, e.g., Aqua, Microsoft Windows (NT/XP), Unix X Windows (KDE, Gnome, and/or the like), and/or the like. The user interface may allow for the display, execution, interaction, manipulation and/or operation of program modules and/or system facilities through textual and/or graphical facilities. The user interface provides a facility through which users may affect, interact and/or operate a computer system. A user interface may communicate to and/or with other modules in a module collection, including itself, and/or facilities of the like. Most frequently, the user interface communicates with operating systems, other program modules and/or the like. The user interface may contain, communicate, generate, obtain and/or provide program module, system, user and/or data communications, requests and/or responses.

Web Browser

A Web browser module 1018 is stored program code that is executed by the CPU. The Web browser may be a conventional hypertext viewing application such as Microsoft Internet Explorer or Netscape Navigator. Secure Web browsing may be supplied with 128-bit (or greater) encryption by way of HTTPS, SSL and/or the like. Some Web browsers allow for the execution of program modules through facilities such as Java, JavaScript, ActiveX and/or the like. Web browsers and like information access tools may be integrated into PDAs, cellular telephones, and/or other mobile devices. A Web browser may communicate to and/or with other modules in a module collection, including itself, and/or facilities of the like. Most frequently, the Web browser communicates with information servers, operating systems, integrated program modules (e.g., plug-ins), and/or the like; e.g., it may contain, communicate, generate, obtain, and/or provide program module, system, user, and/or data communications, requests, and/or responses. Of course, in place of a Web browser and information server, a combined application may be developed to perform similar functions of both. The combined application would similarly affect the obtaining and the provision of information to users, user agents, and/or the like from IDCAP enabled nodes. The combined application may be nugatory on systems employing standard Web browsers.

Cryptographic Server

A cryptographic server module 1019 is stored program code that is executed by the CPU 1003, cryptographic processor 1026, cryptographic processor interface 1029, cryptographic processor device 1028, and/or the like. Cryptographic processor interfaces will allow for expedition of encryption and/or decryption requests by the cryptographic module; however, the cryptographic module, alternatively, may run on a conventional CPU. The cryptographic module allows for the encryption and/or decryption of provided data. The cryptographic module allows for both symmetric and asymmetric (e.g., Pretty Good Protection (PGP)) encryption and/or decryption. The cryptographic module may employ cryptographic techniques such as, but not limited to: digital certificates (e.g., X.509 authentication framework), digital signatures, dual signatures, enveloping, password access protection, public key management and/or the like. The cryptographic module will facilitate numerous (encryption and/or decryption) security protocols such as, but not limited to: checksum, Data Encryption Standard (DES), Elliptical Curve Encryption (ECC), International Data Encryption Algorithm (IDEA), Message Digest 5 (MD5, which is a one way hash function), passwords, Rivest Cipher (RC5), Rijndael, RSA (which is an Internet encryption and authentication system that uses an algorithm developed in 1977 by Ron Rivest, Adi Shamir, and Leonard Adleman), Secure Hash Algorithm (SHA), Secure Socket Layer (SSL), Secure Hypertext Transfer Protocol (HTTPS), and/or the like. Employing such encryption security protocols, the IDCAP controller 801 may encrypt all incoming and/or outgoing communications and may serve as node within a virtual private network (VPN) with a wider communications network. The cryptographic module facilitates the process of "security authorization" whereby access to a resource is inhibited by a security protocol wherein the cryptographic module effects authorized access to the secured resource. In addition, the cryptographic module may provide unique identifiers of content, e.g., employing and MD5 hash to obtain a unique signature for a digital audio file. A cryptographic module may communicate to and/or with other modules in a module collection, including itself, and/or facilities of the like. The cryptographic module supports encryption schemes allowing for the secure transmission of information across a communications network to enable a GVC module to engage in secure transactions if so desired. The cryptographic module facilitates the secure accessing of resources on GVC and facilitates the access of secured resources on remote systems; i.e., it may act as a client and/or server of secured resources. Most frequently, the cryptographic module communicates with information servers, operating systems, other program modules and/or the like. The cryptographic module may contain, communicate, generate, obtain and/or provide program module, system, user and/or data communications, requests and/or responses.

IDCAP Database

A IDCAP database module 1020 may be embodied in a database and its stored data. The database is stored program code, which is executed by the CPU; the stored program code portion configuring the CPU to process the stored data. By way of example only, the IDCAP database may store data associated with captured images 1020A, processed image data 1020B and/or predictive analysis data 820C. The database may be a conventional, fault tolerant, relational, scalable, secure database such as Oracle or Sybase. Relational databases are an extension of a flat file. Relational databases consist of a series of related tables. The tables are interconnected via a key field. Use of the key field allows the combination of the tables by indexing against the key field; i.e., the key fields act as dimensional pivot points for combining information from various tables. Relationships generally identify links maintained between tables by matching primary keys. Primary keys represent fields that uniquely identify the rows of a table in a relational database. More precisely, they uniquely identify rows of a table on the "one" side of a one-to-many relationship.

Alternatively, the IDCAP database may be implemented using various standard data-structures, such as an array, hash, (linked) list, struct, structured text file (e.g., XML), table and/or the like. Such data-structures may be stored in memory and/or in (structured) files. In another alternative, an object-oriented database may be used, such as Frontier, ObjectStore, Poet, Zope and/or the like. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. Also, the database may be implemented as a mix of data structures, objects and relational structures. Databases may be consolidated and/or distributed in countless variations through standard data processing techniques. Portions of databases, e.g., tables, may be exported and/or imported and thus decentralized and/or integrated. In one embodiment, the database module 1020 includes several tables 1020A-1020C. The database module includes other tables and relations as already discussed in FIG. 1 and throughout the disclosure.

In one embodiment, user programs may contain various user interface primitives, which may serve to update IDCAP controller 1001. Also, various accounts may require custom database tables depending upon the environments and the types of clients a IDCAP controller 801 may need to serve. It should be noted that any unique fields may be designated as a key field throughout. In an alternative embodiment, these tables have been decentralized into their own databases and their respective database controllers (i.e., individual database controllers for each of the above tables or other database tables that are not illustrated in FIG. 10, such as the user profile server/database). Employing standard data processing techniques, one may further the databases over several computer systemizations and/or storage devices. Similarly, configurations of the decentralized database controllers may be varied by consolidating and/or distributing the various database modules 1020A-C. The IDCAP controller 1001 may be configured to keep track of various settings, inputs and parameters via database controllers.

A IDCAP database may communicate to and/or with other modules in a module collection, including itself, and/or facilities of the like. Most frequently, the IDCAP database communicates with a IDCAP module, other program modules and/or the like. The database may contain, retain and provide information regarding other nodes and data.

IDCAP Control Module

An IDCAP control module 1035 is stored program code that is executed by the CPU. The IDCAP module 8355 effects execution of the image capture process, the image data analysis and the predictive analysis processes, as well as accessing, obtaining and the provision of information, services, transactions and/or the like across various communications networks.

An IDCAP control module enabling distribution of both sponsored link and banner advertisements may be developed by employing standard development tools such as, but not limited to: (ANSI) (Objective-) C (++), Apache modules, binary executables, database adapter, Java, JavaScript, mapping tools, procedural and object oriented development tools, PERL, Python, shell scripts, SQL commands, web application server extensions, WebObjects, and/or the like. In one embodiment, the IDCAP controller 1001 employs a cryptographic server to encrypt and decrypt communications. An IDCAP control module may communicate to and/or with other modules in a module collection, including itself, and/or facilities of the like. Most frequently, the IDCAP control module communicates with a IDCAP database, operating systems, other program modules and/or the like. The IDCAP control module may contain, communicate, generate, obtain and/or provide program module, system, user and/or data communications, requests and/or responses.

Distributed IDCAP

The structure and/or operation of any of the IDCAP controller components may be combined, consolidated and/or distributed in any number of ways to facilitate development and/or deployment. Similarly, the module collection may be combined in any number of ways to facilitate deployment and/or development. To accomplish this, one may integrate the components into a common code base or in a facility that can dynamically load the components on demand in an integrated fashion.

The module collection may be consolidated and/or distributed in countless variations through standard data processing and/or development techniques. Multiple instances of any one of the program modules in the program module collection may be instantiated on a single node, and/or across numerous nodes to improve performance through load-balancing and/or data-processing techniques. Furthermore, single instances may also be distributed across multiple controllers and/or storage devices; e.g., databases. All program module instances and controllers working in concert may do so through standard data processing communication techniques.

The configuration of the IDCAP will depend on the context of system deployment. Factors such as, but not limited to, the budget, capacity, location and/or use of the underlying hardware resources may affect deployment requirements and configuration. Regardless of if the configuration results in more consolidated and/or integrated program modules, results in a more distributed series of program modules, and/or results in some combination between a consolidated and distributed configuration, data may be communicated, obtained, and/or provided. Instances of modules consolidated into a common code base from the program module collection may communicate, obtain and/or provide data. This may be accomplished through intra-application data processing communication techniques such as, but not limited to: data referencing (e.g., pointers), internal messaging, object instance variable communication, shared memory space, variable passing, and/or the like.

If module collection components are discrete, separate, and/or external to one another, then communicating, obtaining, and/or providing data with and/or to other module components may be accomplished through inter-application data processing communication techniques such as, but not limited to: Application Program Interfaces (API) information passage; (distributed) Component Object Model ((D)COM), (Distributed) Object Linking and Embedding ((D)OLE), and/or the like), Common Object Request Broker Architecture (CORBA), process pipes, shared files, and/or the like. Messages sent between discrete module components for inter-application communication or within memory spaces of a singular module for intra-application communication may be facilitated through the creation and parsing of a grammar. A grammar may be developed by using standard development tools such as lex, yacc, XML, and/or the like, which allow for grammar generation and parsing functionality, which in turn may form the basis of communication messages within and between modules. Again, the configuration will depend upon the context of system deployment.

The entirety of this disclosure (including the Cover Page, Title, Headings, Field, Background, Summary, Brief Description of the Drawings, Detailed Description, Claims, Abstract, Figures, and otherwise) shows by way of illustration various embodiments in which the claimed inventions may be practiced. The advantages and features of the disclosure are of a representative sample of embodiments only, and are not exhaustive and/or exclusive. They are presented only to assist in understanding and teach the claimed principles. It should be understood that they are not representative of all claimed inventions. As such, certain aspects of the disclosure have not been discussed herein. That alternate embodiments may not have been presented for a specific portion of the invention or that further undescribed alternate embodiments may be available for a portion is not to be considered a disclaimer of those alternate embodiments. It will be appreciated that many of those undescribed embodiments incorporate the same principles of the invention and others are equivalent. Thus, it is to be understood that other embodiments may be utilized and functional, logical, organizational, structural and/or topological modifications may be made without departing from the scope and/or spirit of the disclosure. As such, all examples and/or embodiments are deemed to be non-limiting throughout this disclosure. Also, no inference should be drawn regarding those embodiments discussed herein relative to those not discussed herein other than it is as such for purposes of space and reducing repetition. For instance, it is to be understood that the logical and/or topological structure of any combination of any program modules (a module collection), other components and/or any present feature sets as described in the figures and/or throughout are not limited to a fixed operating order and/or arrangement, but rather, any disclosed order is exemplary and all equivalents, regardless of order, are contemplated by the disclosure. Furthermore, it is to be understood that such features are not limited to serial execution, but rather, any number of threads, processes, services, servers, and/or the like that may execute asynchronously, concurrently, in parallel, simultaneously, synchronously, and/or the like are contemplated by the disclosure. As such, some of these features may be mutually contradictory, in that they cannot be simultaneously present in a single embodiment. Similarly, some features are applicable to one aspect of the invention, and inapplicable to others. In addition, the disclosure includes other inventions not presently claimed. Applicant reserves all rights in those presently unclaimed inventions including the right to claim such inventions, file additional applications, continuations, continuations in part, divisions, and/or the like thereof. As such, it should be understood that advantages, embodiments, examples, functional, features, logical, organizational, structural, topological, and/or other aspects of the disclosure are not to be considered limitations on the disclosure as defined by the claims or limitations on equivalents to the claims.

We claim:

1. An optical system for inspecting a moving web of material having a longitudinal axis extending in a direction of travel of the moving web, a transverse axis extending in a direction perpendicular to the longitudinal axis and a plurality of transverse banded regions, the optical system comprising:
    a) a trigger device operatively arranged to detect a transverse banded region on the moving web of material and generate at least one signal upon detecting the transverse banded region to initiate the acquisition of an image of an illuminated portion of the moving web of material having at least one transverse banded region;
    b) an illuminating device in communication with the trigger device and being operatively arranged to illuminate a portion of the moving web of material having at least one transverse banded region in response to a signal generated by the trigger device; and
    c) an image capturing device in communication with the trigger device and being operatively arranged to acquire an image of a portion of the moving web of material having at least one transverse banded region in a field of view illuminated by the illuminating device in response to a signal generated by the trigger device; and
    d) a processing unit in communication with the image capturing device and operatively arranged to:
        (i) analyze images acquired by the image capturing device;
        (ii) ascertain a width of at least one of the transverse banded regions of the moving web of material based on the analyses of the images acquired by the image capturing device; and
        (iii) determine the reduced ignition propensity characteristic of a population of smoking articles having a wrapper formed from the moving web of material based on an analysis of the width of at least one of the transverse banded regions of the moving web of material.

2. The optical system according to claim 1, wherein the trigger device comprises an encoder device adapted to detect transverse banded regions on the moving web of material.

3. The optical system according to claim 2, wherein the encoder device comprises a LED encoder sensor which conducts coarse reflectivity analysis of the moving band of material.

4. The optical system according to claim 1, wherein the image capturing device is operatively arranged to acquire an image of a portion of the moving web of material having at least one transverse banded region when a transverse banded region is disposed at or about the center of the field of view of the image capturing device.

5. The optical system according to claim 4, wherein the transverse banded region disposed at or about the center of the field of view of the image capturing device is the transverse banded region detected by the trigger device to generate the signal which initiates the acquisition of the image.

6. The optical system according to claim 1, wherein the trigger device is disposed upstream of the image capturing device relative to the direction of travel of the moving web of material.

7. The optical system according to claim 6, wherein the trigger device comprises a sensor which is positioned a distance from the center of the field of view of the image capturing device comprising a multiple of a whole number of a distance between the centers of adjacent transverse banded regions on the moving web of material.

8. The optical system according to claim 1, wherein the illuminating device comprises an annular housing and a plurality of light emitting diodes arranged in a single row on the housing.

9. The optical system according to claim 8, wherein the plurality of light emitting diodes comprises a strobe light.

10. The optical system according to claim 9, wherein the light emitted from the strobe light has a low angle of incidence relative to the moving web of material.

11. The optical system according to claim 9, wherein the light emitted from the strobe light has an angle of incidence of approximately 0 degrees relative to the moving web of material.

12. The optical system according to claim 1, wherein the illuminating device comprises two sets of light emitting diodes disposed on opposite sides of a longitudinal centerline of the moving web of material.

13. The optical system according to claim 12, wherein each set of light emitting diodes extends in a direction parallel to the longitudinal axis of the moving web of material.

14. The optical system according to claim 13, wherein each set of light emitting diodes comprises a strobe light.

15. The optical system according to claim 14, wherein the light emitted from the strobe light has a low angle of incidence relative to the moving web of material.

16. The optical system according to claim 14, wherein the light emitted from the strobe light has an angle of incidence of approximately 0 degrees relative to the moving web of material.

17. The optical system according to claim 1, wherein the image capture device comprises a high resolution camera suitable for high speed image acquisition.

18. The optical system according to claim 14, wherein the camera comprises a CCD array for acquiring an image of a portion of the moving web of material.

19. The optical system according to claim 1, wherein the processing unit is further operatively arranged to store data derived from the analysis of images acquired by the image capturing device.

20. The optical system according to claim 1, further comprising a controller in communication with the trigger device and at least one of the illuminating device and image capturing device, wherein the controller is operatively arranged to receive a signal generated by the trigger device and, in response to the signal, actuate the illuminating device to illuminate a portion of the moving web of material having at least one transverse banded region and/or the image capturing device to acquire an image of an illuminated portion of the moving web of material having at least one transverse banded region.

21. The optical system according to claim 1, wherein the trigger device is operatively arranged to generate at least one signal upon detecting the transverse banded region to actuate the illuminating device to illuminate a portion of the moving web of material having at least one transverse banded region and the image capturing device to acquire an image of an illuminated portion of the moving web of material having at least one transverse banded region.

22. A method for inspecting a moving web of material having a longitudinal axis extending in a direction of travel of the moving web, a transverse axis extending in a direction perpendicular to the longitudinal axis and plurality of transverse banded regions, comprising:
   a) detecting a transverse banded region on the moving web of material;
   b) generating at least one signal upon detecting a transverse banded region to initiate the illumination and acquisition of a portion of the moving web of material having at least one transverse banded region;
   c) illuminating a field of view containing a portion of the moving web of material having at least one transverse banded region;
   d) acquiring an image of the illuminated field of view containing a portion of the moving web of material having at least one transverse banded region; and
   e) processing the acquired image in a processing unit to ascertain a width of at least one of the transverse banded regions on the moving web of material and determine the reduced ignition propensity characteristics of a population of smoking articles having a wrapper formed from the moving web of material based on the width of at least one transverse banded region on the moving web of material.

23. The method according to claim 22, wherein the step of acquiring the image of the illuminated field of view containing a portion of the moving web of material comprises recording on an array of imaging pixels the intensities of the light reflected off the moving web of material during the illuminating step.

24. The method according to claim 23, wherein the processing step comprises:
   a) creating a two dimensional gray-scale matrix by assigning a gray-scale value for each imaging pixel based on the intensity of the light recorded on the imaging pixel;
   b) converting the two dimensional gray-scale matrix to one dimensional projection data;
   c) applying a predetermined threshold parameter to identify leading and trailing edges of transverse banded regions on the moving web of material;
   d) comparing the threshold parameter with the one dimensional projection data to determine the locations of leading and trailing edges of the transverse banded regions on the moving web of material;
   e) calculating the width of the transverse banded region based on the locations of the leading and trailing edges on the moving web of material;
   f) determining the mode and standard deviation values of the calculated widths of a plurality of the transverse banded regions on the moving web of material; and
   g) comparing the mode and standard deviation values of the calculated widths of the transverse banded regions on the moving web of material with mode and standard deviation values of widths of transverse banded regions on a web of material which is slitted to form wrapping papers for a population of smoking articles having acceptable reduced ignition propensity and freeburn characteristics.

25. The method according to claim 24, wherein the processing step further includes the step of filtering the one dimensional projection data to decrease the effect of interference or noise captured on the acquired image.

26. A method of measuring a width of a transverse banded region on a moving web of material, comprising:
   a) illuminating a field of view containing a portion of the moving web of material having at least one transverse banded region;
   b) acquiring an image comprising a plurality of imaging pixel of the illuminated field of view containing a portion of the moving web of material having at least one transverse banded region;
   c) creating a two dimensional gray-scale matrix by assigning a gray-scale value for each imaging pixel based on the intensity of the light recorded on the imaging pixel;
   d) converting the two dimensional gray-scale matrix to one dimensional projection data;
   e) applying a predetermined threshold parameter to identify leading and trailing edges of transverse banded regions on the moving web of material;
   f) comparing the threshold parameter with the one dimensional projection data to determine the locations of leading and trailing edges of the transverse banded regions on the moving web of material; and
   g) calculating the width of the transverse banded region based on the locations of the leading and trailing edges on the moving web of material.

* * * * *